(12) United States Patent
Xing et al.

(10) Patent No.: US 10,087,212 B2
(45) Date of Patent: Oct. 2, 2018

(54) CRYSTAL FORM OF ABIRATERONE PROPIONATE AND PREPARATION METHOD THEREFOR

(71) Applicant: CHONGQING PHARMACEUTICAL RESEARCH INSTITUTE CO., LTD, Chongqing (CN)

(72) Inventors: Naiguo Xing, Chongqing (CN); Yan Shangguan, Chongqing (CN); Deping Zheng, Chongqing (CN); Fanglu Chen, Chongqing (CN)

(73) Assignee: CHONGQING PHARMACEUTICAL RESEARCH INSTITUTE CO., LTD, Chongqing (CN)

( * ) Notice: Subject to any disclaimer, the term of this patent is extended or adjusted under 35 U.S.C. 154(b) by 0 days.

(21) Appl. No.: 15/551,185

(22) PCT Filed: Feb. 3, 2016

(86) PCT No.: PCT/CN2016/073254
§ 371 (c)(1),
(2) Date: Aug. 15, 2017

(87) PCT Pub. No.: WO2016/127876
PCT Pub. Date: Aug. 18, 2016

(65) Prior Publication Data
US 2018/0030085 A1    Feb. 1, 2018

(30) Foreign Application Priority Data
Feb. 15, 2015 (CN) .......................... 2015 1 0080991

(51) Int. Cl.
*C07J 43/00* (2006.01)

(52) U.S. Cl.
CPC .......... *C07J 43/003* (2013.01); *C07B 2200/13* (2013.01)

(58) Field of Classification Search
CPC ........................................................ C07J 43/00
See application file for complete search history.

(56) References Cited

FOREIGN PATENT DOCUMENTS

| CN | 101768199 A | | 7/2010 |
| CN | 104710498 | * | 6/2015 |
| CN | 104710499 A | | 6/2015 |
| WO | 2014111815 A2 | | 7/2014 |

OTHER PUBLICATIONS

International Search Report for PCT/CN2016/073254, dated Apr. 29, 2016, ISA/CN.

* cited by examiner

*Primary Examiner* — Sun Jae Yoo
(74) *Attorney, Agent, or Firm* — U.S. Fairsky LLP; Yue (Robert) Xu

(57) ABSTRACT

The present invention relates to the field of pharmaceutical chemistry, and particularly to a crystal form of Abiraterone propionate and a preparation method therefor. Characteristic diffraction peaks occur at positions, where the 2θ value is 5.7°, 11.9°, 12.4°, 14.9°, 15.8°, 16.7°, 18.5°, 19.1°, 21.7°, 22.4°, and 39.9°±0.2°, in an X-ray powder diffraction spectrum of the crystal form of Abiraterone propionate.

7 Claims, 1 Drawing Sheet

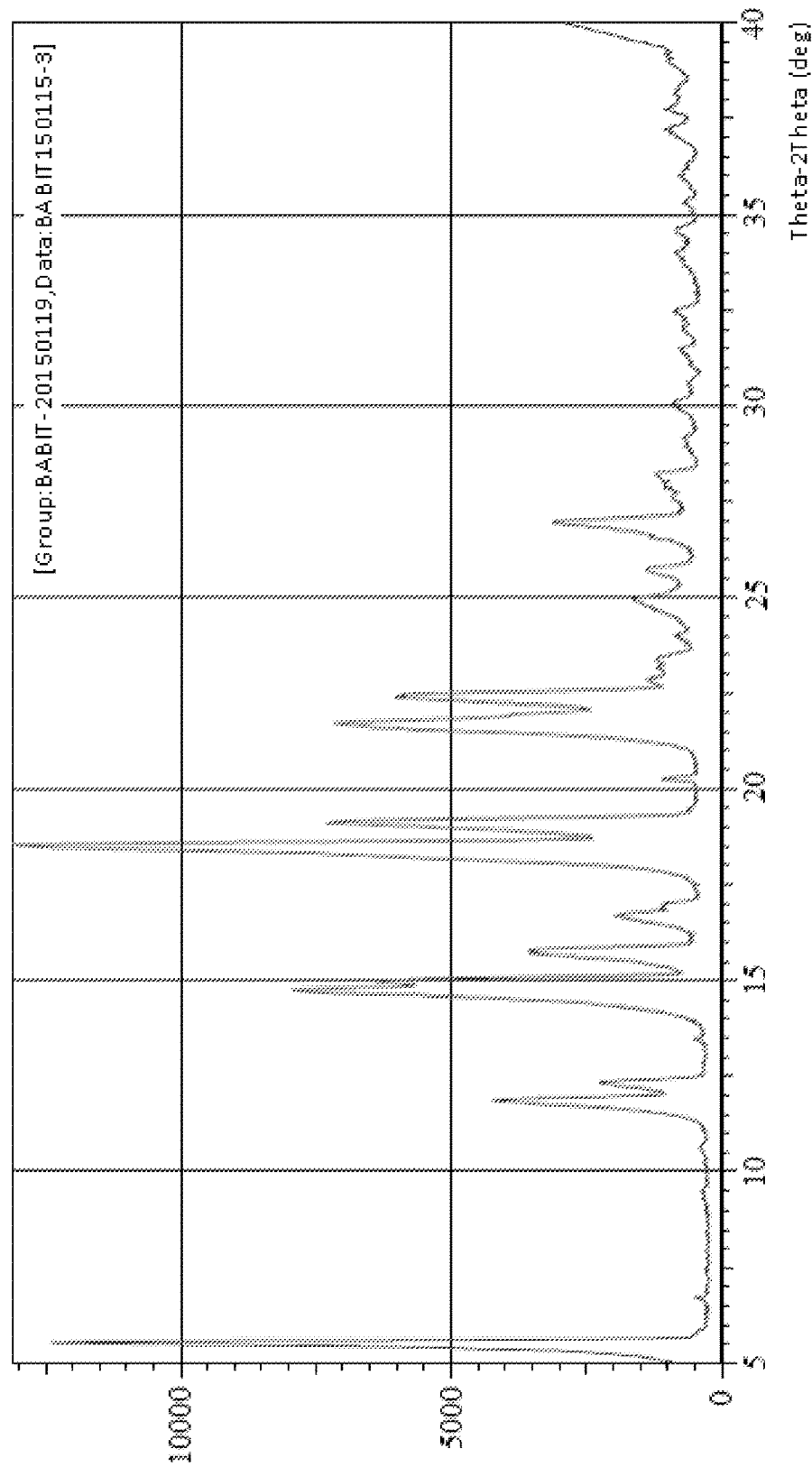

CRYSTAL FORM OF ABIRATERONE PROPIONATE AND PREPARATION METHOD THEREFOR

This application is the national phase of International Application No. PCT/CN2016/073254, titled "CRYSTAL FORM OF ABIRATERONE PROPIONATE AND PREPARATION METHOD THEREFOR", filed on Feb. 3, 2016, which claims the priority of Chinese Patent Application No. 201510080991.3, filed with Chinese Patent Office on Feb. 15, 2015, titled with "CRYSTAL FORM OF ABIRATERONE PROPIONATE AND PREPARATION METHOD THEREFOR", and the disclosure of which is hereby incorporated by reference.

FIELD

The present disclosure relates to the field of pharmaceutical chemistry, and particularly to a crystal form of Abiraterone propionate and a preparation method therefor.

BACKGROUND

Androgen can promote the growth of prostate cancer cells. At present, the first choice of treatment for advanced prostate cancer patients is castration treatment including drugs and surgery to reduce the synthesis of androgen by testis, but this treatment cannot inhibit other parts of the body from producing androgen. Abiraterone acetate (Formula II) was marketed in the United States in April and Europe in September, 2011 for the treatment of advanced prostate cancer. Because Abiraterone acetate treatment is an endocrine therapy, which can inhibit testis and other parts of the body from producing androgen, therefore compared with the current conventional treatments, it has a better efficacy, lower side effects, creating a new field of anti-androgen therapy.

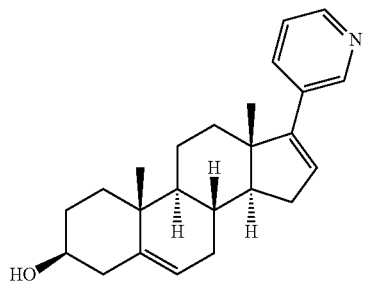

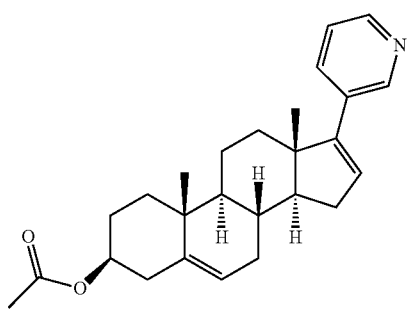

Abiraterone acetate exerts its pharmacological effects by convertion to Abiraterone (Formula III) in vivo. Abiraterone is an inhibitor to cytochrome oxidase P450 (CYP450) c17, which reduces the androgen level by inhibiting the key enzyme, CYP450c17, in androgen synthesis. Therefore, Abiraterone not only has inhibition effect androgen produced by testis, but also by other parts of the body such as adrenal gland.

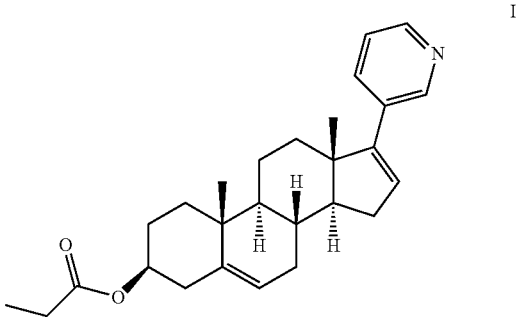

Abiraterone propionate is a homologue of Abiraterone acetate, of which the chemical name is (3β)-17-(3-pyridyl)-androstane-5,16-dien-3-ol propionate, and the structure is represented by Formula I.

WO2014111815A2 discloses Abiraterone propionate. Similar to Abiraterone acetate, Abiraterone propionate can be converted to Abiraterone in vivo and plays its pharmacological effects. At present, there is no report on crystal form of Abiraterone propionate. Therefore, it is important to study the crystal form of Abiraterone propionate.

SUMMARY

An object of the present disclosure is to provide a crystal form of Abiraterone propionate, which is defined herein as crystal form A of Abiraterone propionate. The crystal form A is stable and suitable for the production of various dosage forms.

The X-ray powder diffraction pattern of the crystal form A of Abiraterone propionate provided in the present disclosure has characteristic diffraction peaks at 2θ±0.2°, and the 2θ is 5.7°, 11.9°, 12.4°, 14.9°, 15.8°, 16.7°, 18.5°, 19.1°, 21.7°, 22.4°, 39.9°.

The X-ray powder diffraction pattern of the crystal form A of Abiraterone propionate of the present disclosure has characteristic diffraction peaks substantially as shown in FIG. 1.

In a specific embodiment, the X-ray powder diffraction pattern of the crystal form A of Abiraterone propionate of the present disclosure has corresponding diffraction peaks at 2θ position which is 5.3°, 5.7°, 11.9°, 12.4°, 14.2°, 14.9°, 15.8°, 16.7°, 17.0°, 18.5°, 19.1°, 20.3°, 21.7°, 22.4°, 22.9°, 23.4°, 24.9°, 25.7°, 26.9°, 27.6°, 27.9°, 28.2°, 30.0°, 32.4°, 34.6°, 37.1°, 37.8°, 39.1° and 39.9°±0.2°.

Another object of the present disclosure is to provide a method for preparing the crystal form A of Abiraterone propionate, comprising: dissolving Abiraterone propionate in an appropriate organic solvent; performing crystallization under stirring; and separating.

In an embodiment, the method for preparing the crystal form A of Abiraterone propionate of the present disclosure comprises the following steps:

a) dissolving Abiraterone propionate in an appropriate organic solvent;

b) performing cooling crystallization under stirring and/or crystallization by adding a poor solvent;

c) separating solid.

In another embodiment, the method for preparing the crystal form A of Abiraterone propionate of the present disclosure comprises the following steps:

a) dissolving Abiraterone propionate in an appropriate organic solvent;

b) performing cooling crystallization under stirring and/or crystallization by adding a poor solvent;

c) separating solid; and d) drying the separated solid.

In the above-mentioned embodiments, the appropriate organic solvent in step a) of the method in the present disclosure includes methanol, ethanol, isopropanol, acetone, ethyl acetate, methyl acetate, dichloromethane, chloroform, acetonitrile, tetrahydrofuran, n-heptane or a mixture thereof; preferably methanol, ethanol, isopropanol, acetone, ethyl acetate, acetonitrile or n-heptane.

In step a), the temperature at which Abiraterone propionate is dissolved is from 0° C. to the boiling point of the solvent.

In step b), the poor solvent refers to a solvent in which Abiraterone propionate has a poor solubility and which is miscible with a solvent in which Abiraterone propionate is dissolved at room temperature.

In the above-mentioned embodiments, in step b) of the method of the present disclosure, cooling crystallization and crystallization by adding a poor solvent can be used singly or as a combination thereof.

In a specific embodiment, the method for preparing the crystal form A of Abiraterone propionate of the present disclosure comprises:

a) dissolving Abiraterone propionate in an appropriate organic solvent;

the temperature for dissolution is from 0° C. to boiling point of the solvent;

wherein, the appropriate organic solvent includes methanol, ethanol, isopropanol, acetone, ethyl acetate, methyl acetate, dichloromethane, chloroform, acetonitrile, tetrahydrofuran, n-heptane or a mixture thereof;

b) performing cooling crystallization under stirring and/or crystallization by adding a poor solvent;

The end temperature of the cooling is generally at least 10° C. lower than the temperature for dissolution;

preferably, the end temperature of the cooling is at least 30° C. lower than the temperature for dissolution;

more preferably, the end temperature of the cooling is at least 50° C. lower than the temperature for dissolution;

the poor solvent refers to a solvent in which Abiraterone propionate has a poor solubility and which is miscible with a solvent in which Abiraterone propionate is dissolved at room temperature;

when the solvent for dissolving Abiraterone propionate is methanol, ethanol, isopropanol, acetone, acetonitrile, tetrahydrofuran or the like, or a mixture thereof, the poor solvent includes water, lower alkane (such as n-hexane, petroleum ether, cyclohexane, n-pentane, n-heptane, etc.), methyl tert-butyl ether and the like;

when the solvent for dissolving Abiraterone propionate is ethyl acetate, methyl acetate, dichloromethane, chloroform or the like, or a mixture thereof, the poor solvent includes lower alkane (such as n-hexane, petroleum ether, cyclohexane, n-pentane, n-heptane, etc.), methyl tert-butyl ether and the like;

The feeding mode can be adding the poor solvent to a solution of Abiraterone acetateor adding a solution of Abiraterone acetate to the poor solvent;

the cooling crystallization and crystallization by adding a poor solvent can be used singly or as a combination thereof;

c) separating, including filtration or centrifugation to collect precipitated solid;

d) drying the separated solid;

the drying temperature is generally 20~100° C.;

preferably, the drying temperature is 25~80° C.;

The drying can be performed under atmospheric pressure or reduced pressure.

The present disclosure also provides a pharmaceutical composition which comprises the crystal form A of Abiraterone propionate of the present disclosure and a pharmaceutically acceptable excipient.

The pharmaceutically acceptable excipient in the pharmaceutical composition of the present disclosure is conventional excipient in the art and the preparation method thereof is also conventional method in the art, which are not repeated herein.

The dosage form of the pharmaceutical composition of the present disclosure may be oral preparation, injection or external preparation, and the like, wherein the oral preparation may be tablet, capsule, pill, granule, slow release or controlled release tablet or capsule, and the like. These dosage forms may be prepared by conventional excipients and corresponding conventional methods in the art.

The crystal form A of Abiraterone propionate of the present disclosure has stable physical and chemical properties, suitable for long-term storage and manufacture process of a preparation thereof. The crystal form A of Abiraterone propionate of the present disclosure can be used in the manufacture of a medicament for treating prostate cancer.

BRIEF DESCRIPTION OF DRAWING

FIG. 1 shows X-ray powder diffraction pattern of the crystal form A of Abiraterone propionate.

DETAILED DESCRIPTION

The present disclosure will be described in further detail with reference to examples which are not intended to limit the scope of the present disclosure in any way, so that the present disclosure can be understood more fully by those skilled in the art.

The X-ray powder diffraction analysis in the present disclosure was carried out at the ambient temperature and the ambient humidity by a CuKα source (α=1.5406 Å) of XRD-6000 type X-ray diffractometer (Shimadzu, Japan). "Ambient temperature" is generally 0~40° C.; "ambient humidity" is generally 30~80% relative humidity.

Abiraterone used below can be prepared by the methods disclosed in patent GB 2265624 and WO95/09178.

Example 1

Preparation of Abiraterone Propionate 10 g of Abiraterone, 100 ml of dichloromethane, 6 g of propionic anhydride, and 100 mg of 4-dimethylaminopyridine were added to a 250 ml reaction flask and stirred at room temperature for 4~6 hours. After completion of the reaction, 50 ml of water was added and the pH was adjusted to 9 with a 5% sodium carbonate solution. The organic layer was separated, washed with 100 ml water twice and 100 ml saturated brine once, and then concentrated to dry under reduced pressure. 100 ml of ethanol was added to the residue; the mixture was heated to reflux to dissolve it completely; 100 ml purified water was added and the mixture was cooled to room temperature; filtration was performed and the filtrate was dried at 60° C. under reduced pressure to obtain 11 g of Abiraterone propionate.

Example 2

Preparation of Crystal Form A of Abiraterone Propionate 1 g of Abiraterone propionate prepared in Example 1 and 5 ml of acetonitrile were added to a 10 ml reaction flask; the mixture was heated to reflux to dissolve it completely and then cooled to a temperature lower than 10° C. for crystallization; filtration was performed and the resulting solid was dried at 50~60° C. under reduced pressure to obtain crystal form A of Abiraterone propionate. The obtained crystal form A was subjected to X-ray powder diffraction test and the X-ray powder diffraction pattern is shown in FIG. 1, the measured values are shown in the following table.

TABLE 1

Data of X-ray powder diffraction pattern of crystal form A of Abiraterone propionate.

| 2θ (°) | d (Å) | relative strength (%) | 2θ (°) | d (Å) | relative strength (%) |
|---|---|---|---|---|---|
| 5.3 | 16.61 | 4 | 5.7 | 15.57 | 73 |
| 11.9 | 7.43 | 29 | 12.4 | 7.15 | 15 |
| 14.2 | 6.25 | 4 | 14.9 | 5.96 | 57 |
| 15.8 | 5.62 | 25 | 16.7 | 5.30 | 11 |
| 17.0 | 5.20 | 4 | 18.5 | 4.79 | 100 |
| 19.1 | 4.64 | 53 | 20.3 | 4.34 | 3 |
| 21.7 | 4.09 | 52 | 22.4 | 3.96 | 44 |
| 22.9 | 3.88 | 6 | 23.4 | 3.80 | 5 |
| 24.9 | 3.57 | 8 | 25.7 | 3.46 | 7 |
| 26.9 | 3.30 | 21 | 27.6 | 3.23 | 3 |
| 27.9 | 3.19 | 4 | 28.2 | 3.16 | 6 |
| 30.0 | 2.97 | 3 | 32.4 | 2.76 | 3 |
| 34.6 | 2.59 | 3 | 37.1 | 2.42 | 4 |
| 37.8 | 2.38 | 4 | 39.1 | 2.30 | 3 |
| 39.9 | 2.26 | 17 | — | — | — |

Example 3

Preparation of Crystal Form A of Abiraterone Propionate 1 g of Abiraterone propionate prepared in Example 1 and 10 ml of absolute ethanol were added to a 50 ml reaction flask and dissolved at 60° C.; 10 ml purified water was added dropwise with stirring to precipitate the product; the mixture was warmed and stirred at 60° C. for 1 hour, and then cooled slowly to 10~20° C. for crystallization; filtration was performed and the resulting solid was dried at 50~60° C. under reduced pressure to obtain the crystal form A of Abiraterone propionate.

Example 4

Preparation of Crystal Form A of Abiraterone Propionate 1 g of Abiraterone propionate crystal form A prepared in Example 1 and 4 ml of ethyl acetate were added to a 250 ml reaction flask and dissolved at 20~30° C.; 20 ml petroleum ether was added for crystallization; filtration was performed and the resulting solid was dried at 50~60° C. under reduced pressure to obtain the crystal form A of Abiraterone propionate.

Example 5

Preparation of Crystal Form A of Abiraterone Propionate 1 g of Abiraterone propionate prepared in Example 1 and 5 ml of isopropyl alcohol were added to a 10 ml reaction flask; the mixture was heated to reflux to dissolve it completely and then cooled to a temperature lower than 10° C. for crystallization; filtration was performed and the resulting solid was dried at 50~60° C. under reduced pressure to obtain the crystal form A of Abiraterone propionate.

Example 6

Preparation of Crystal Form A of Abiraterone Propionate 1 g of Abiraterone propionate prepared in Example 1 and 10 ml of N-heptane were added to a 10 ml reaction flask; the mixture was heated to reflux to dissolve it completely and then cooled to a temperature lower than 10° C. for crystallization; filtration was performed and the resulting solid was dried at 50~60° C. under reduced pressure to obtain the crystal form A of Abiraterone propionate.

Example 7

Preparation of Crystal Form A of Abiraterone Propionate 1 g of Abiraterone propionate prepared in Example 1 and 10 ml of methanol were added to a 50 ml reaction flask and dissolved at 60° C.; 20 ml purified water was added dropwise with stirring to precipitate the product; the mixture was stirred at 60° C. for 1 hour, and then cooled to 10~20° C. for crystallization; filtration was performed and the resulting solid was dried at 50~60° C. under reduced pressure to obtain the crystal form A of Abiraterone propionate.

Example 8

Preparation of Crystal Form A of Abiraterone Propionate 1 g of Abiraterone propionate prepared in Example 1 and 5 ml of acetone were added to a 10 ml reaction flask; the mixture was heated to reflux to dissolve it completely and then cooled to a temperature lower than 10° C. for crystallization; filtration was performed and the resulting solid was dried at 50~60° C. under reduced pressure to obtain the crystal form A of Abiraterone propionate.

The crystal form A of Abiraterone propionate obtained in Examples 3 to 8 were subjected to X-ray powder diffraction test, and all showed the characteristic peaks as shown in FIG. 1.

Example 9

Stability Test

The crystal forms obtained in Examples 2 to 4 were placed under an environment having a temperature of 40±2° C. and a humidity of RH 75±5% for 3 months. The melting point, specific optical rotation, purity and crystal appearance were measured on 0 day, 1-month, 2-month and 3-month, respectively. The results are shown in Table 2.

TABLE 2

Results of the stability test of crystal forms in Examples 2 to 4.

| Example | Test item | 0 month | 1 month | 2 months | 3 months |
|---|---|---|---|---|---|
| Example 2 | Melting point | 109.5~110.4° C. | 109.4~110.3° C. | 109.4~110.5° C. | 109.8~110.5° C. |
|  | Specific optical rotation | −44.32° | −44.06° | −43.67° | −44.23° |
|  | Purity | 99.88 | 99.86 | 99.82 | 99.81 |
|  | Crystal appearance | No change | No change | No change | No change |
| Example 3 | Melting point | 109.7~110.6° C. | 109.4~110.4° C. | 109.5~110.0° C. | 109.8~110.6° C. |
|  | Specific optical rotation | −44.34° | −44.21° | −44.05° | −43.99° |
|  | Purity | 99.89 | 99.87 | 99.84 | 99.82 |
|  | Crystal appearance | No change | No change | No change | No change |
| Example 4 | Melting point | 109.6~110.5° C. | 109.4~110.4° C. | 109.5~110.7° C. | 109.7~110.6° C. |
|  | Specific optical rotation | −44.46° | −44.13° | −44.08° | −43.92° |
|  | Purity | 99.86 | 99.83 | 99.81 | 99.79 |
|  | Crystal appearance | No change | No change | No change | No change |

The results of experiments shown in Table 2 demonstrated that the crystal form of Abiraterone propionate of the present disclosure has good stability and no crystal transformation occurred.

The present disclosure has been described in detail, including preferred embodiments. It should be understood, however, that those skilled in the art can make modifications and/or improvements within the spirit and scope of the present invention in view of the teachings of the present disclosure, which are within the scope of the present invention.

The invention claimed is:

1. A crystal form A of Abiraterone propionate, wherein X-ray powder diffraction pattern thereof has characteristic diffraction peaks at 2θ±0.2°, and the 2θ is 5.7°, 11.9°, 12.4°, 14.9°, 15.8°, 16.7°, 18.5°, 19.1°, 21.7°, 22.4°, and 39.9°.

2. The crystal form A of claim 1, wherein the X-ray powder diffraction pattern has a diffraction peaks at 2θ±0.2°, and the 2θ is 5.3°, 5.7°, 11.9°, 12.4°, 14.2°, 14.9°, 15.8°, 16.7°, 17.0°, 18.5°, 19.1°, 20.3°, 21.7°, 22.4°, 22.9°, 23.4°, 24.9°, 25.7°, 26.9°, 27.6°, 27.9°, 28.2°, 30.0°, 32.4°, 34.6°, 37.1°, 37.8°, 39.1°, and 39.9°.

3. A method for preparing the crystal form A of Abiraterone propionate, comprising the following steps:
a) dissolving Abiraterone propionate in an organic solvent;
b) performing cooling crystallization under stirring and/or crystallization by adding a poor solvent; and
c) separating solid.

4. The method according to claim 3, wherein the organic solvent is selected from methanol, ethanol, isopropanol, acetone, ethyl acetate, methyl acetate, dichloromethane, chloroform, acetonitrile, tetrahydrofuran and n-heptane, or a mixture thereof.

5. The method according to claim 3, wherein the temperature at which Abiraterone propionate is dissolved in step a) is from 0° C. to boiling point of the solvent.

6. The method according to claim 3, wherein a further step of drying the separated solid after step c) is included.

7. A pharmaceutical composition, comprising the crystal form A of Abiraterone propionate according to claim 1 and a pharmaceutically acceptable excipient.

* * * * *